US009078787B2

(12) United States Patent
Gehling et al.

(10) Patent No.: US 9,078,787 B2
(45) Date of Patent: Jul. 14, 2015

(54) SHUTTER PRESS COMPRESSOR WITH SHAPING ELEMENTS

(71) Applicant: Kimberly-Clark Worldwide, Inc., Neenah, WI (US)

(72) Inventors: Steven Craig Gehling, Oshkosh, WI (US); Charles Robert Tomsovic, Omro, WI (US)

(73) Assignee: Kimberly-Clark Worldwide, Inc., Neenah, WI (US)

( * ) Notice: Subject to any disclaimer, the term of this patent is extended or adjusted under 35 U.S.C. 154(b) by 398 days.

(21) Appl. No.: 13/630,377

(22) Filed: Sep. 28, 2012

(65) Prior Publication Data

US 2014/0093604 A1   Apr. 3, 2014

(51) Int. Cl.
*A61F 13/20* (2006.01)
*D04H 1/22* (2006.01)
*B29C 43/02* (2006.01)

(52) U.S. Cl.
CPC ......... *A61F 13/2037* (2013.01); *A61F 13/2031* (2013.01); *A61F 13/2034* (2013.01); *A61F 13/2088* (2013.01); *A61F 13/2091* (2013.01); *B29C 43/021* (2013.01); *B29C 2043/023* (2013.01)

(58) Field of Classification Search
CPC ......... A61F 13/2088; B30B 5/00; B30B 7/00; B30B 7/04; B30B 15/026; B30B 11/08; B30B 15/02; B30B 9/00; B29C 43/23; B29C 43/021; B29C 2043/023
USPC ............ 28/118, 119, 120; 100/223, 224, 232, 100/233; 425/330
See application file for complete search history.

(56) References Cited

U.S. PATENT DOCUMENTS

| 2,133,675 | A |   | 10/1938 | Ten Bosch |
| 2,263,909 | A |   | 11/1941 | Webb |
| 2,425,004 | A | * | 8/1947 | Rabell ............................. 28/118 |
| 2,798,260 | A |   | 7/1957 | Niepmann et al. |
| 3,093,862 | A |   | 6/1963 | Gerard et al. |
| 3,231,935 | A |   | 2/1966 | Brayman |
| 3,270,502 | A |   | 9/1966 | Wentorf, Jr. |
| 3,457,593 | A |   | 7/1969 | Basset |

(Continued)

FOREIGN PATENT DOCUMENTS

| DE | 1 035 352 B | 7/1958 |
| DE | 1 767 561 B1 | 10/1974 |

(Continued)

*Primary Examiner* — Amy Vanatta

(74) *Attorney, Agent, or Firm* — Kimberly-Clark Worldwide, Inc.

(57) ABSTRACT

An apparatus for compressing a material includes a central longitudinal axis, a plurality of levers, and a plurality of jaws, wherein each jaw is attached to a lever, and wherein each jaw has a compression surface having an area. The apparatus also includes a compressing mechanism configured to move each lever in a non-linear motion such that the area of a compression surface exposed to the material decreases with the inward movement of that compression surface; and a shaping element associated with at least one compression surface. The apparatus can include a plurality of shaping elements projecting from at least one compression surface, wherein the plurality of shaping elements is configured to impart a pattern in the material. The apparatus can include a plurality of shaping elements each projecting from a compression surface, wherein the plurality of shaping elements is configured to impart a plurality of grooves in the material.

19 Claims, 12 Drawing Sheets

(56) References Cited

U.S. PATENT DOCUMENTS

| | | | |
|---|---|---|---|
| 3,640,665 A * | 2/1972 | Seefluth | 425/297 |
| 4,109,354 A | 8/1978 | Ronc | |
| 4,208,174 A | 6/1980 | Taricco | |
| 4,498,218 A | 2/1985 | Friese | |
| 4,951,368 A | 8/1990 | Heinen | |
| 5,592,725 A | 1/1997 | Brinker | |
| 5,813,102 A * | 9/1998 | Leutwyler et al. | 28/118 |
| 5,909,884 A * | 6/1999 | Schwankhart | 28/118 |
| 6,022,206 A | 2/2000 | McNutt | |
| 6,310,269 B1 | 10/2001 | Friese et al. | |
| 7,967,803 B2 | 6/2011 | Van Ingelgem et al. | |
| 2002/0151859 A1 | 10/2002 | Schoelling | |
| 2010/0299896 A1 | 12/2010 | Schoelling | |
| 2012/0137479 A1 * | 6/2012 | Rolli et al. | 28/118 |
| 2012/0187600 A1 | 7/2012 | Graber | |

FOREIGN PATENT DOCUMENTS

| | | |
|---|---|---|
| DE | 2 446 959 A1 | 4/1976 |
| DE | 2 520 329 A1 | 5/1977 |
| EP | 1 022 004 B1 | 12/2003 |
| EP | 2 179 828 A1 | 4/2010 |
| EP | 1 304 094 B1 | 3/2011 |
| FR | 1 178 560 A | 5/1959 |
| GB | 1 004 165 A | 9/1965 |
| JP | 2002-512543 A | 4/2002 |
| WO | WO 90/09274 A1 | 8/1990 |
| WO | WO 00/53141 A1 | 9/2000 |

\* cited by examiner

SHUTTER PRESS COMPRESSOR WITH SHAPING ELEMENTS

BACKGROUND

Radial presses are currently used to compress materials for reasons including the addition of stability, the reduction of volume, and the addition of shape to the material. An uncompressed sample of material is inserted into a press, and jaws are moved inwardly in a radial direction to compress the material. Spaces between jaws are required to allow the jaws to move inwardly over a limited range without interfering with neighboring jaws. Because of this design, however, material can migrate into the spaces between the radius jaws of prior presses during compression. This can cause the material or product to become aesthetically unacceptable, limited in expected performance, or even dangerous. In addition, portions of the material or product can become bent, pinched, torn, deformed, or raised during manufacture of the product.

In a specific example, tampons are initially formed in a non-compressed state using various absorbent materials in a flat configuration. To make a tampon pledget that is of a suitable shape and integrity for insertion, the uncompressed absorbent materials must be folded, rolled, or stacked in such a manner to allow the uncompressed absorbent materials or blank to be inserted into a tampon compression apparatus or press. This press reduces the volume of the absorbent material until sufficient compression occurs and the blank is temporarily deformed into a tampon pledget that can be inserted into the vaginal cavity to absorb various body fluids including menses. In addition, modern tampon designs can include a secondary absorbent structure such as petals that are designed to migrate in a radial direction from the tampon pledget. Such petals can become bent, pinched, torn, deformed, or raised during manufacture of the product. Further, insufficient compression can prevent a used tampon from remaining fully intact as it is withdrawn; the tampon can substantially delaminate, unroll, unfold, telescope, or otherwise structurally degrade.

To combat these structural issues, numerous attempts to stabilize compressed material have been undertaken. For example, some have tried binder fibers, adhesives, grooved compression, needling, microwave radiation, and the like. However, despite these efforts, there still exists a need for compressed materials to have greater stability during storage and use.

SUMMARY

In one aspect, the present disclosure provides an apparatus for compressing a material, the apparatus having a central longitudinal axis and including a plurality of levers and a plurality of jaws, wherein each jaw is attached to a lever, and wherein each jaw has a compression surface having an area. The apparatus also includes a compressing mechanism configured to move each lever in a non-linear motion such that the area of a compression surface exposed to the material decreases with the inward movement of that compression surface; and a shaping element associated with at least one compression surface.

In another aspect, the present disclosure provides an apparatus for compressing a material, the apparatus having a central longitudinal axis and including a plurality of levers and a plurality of jaws, wherein each jaw is attached to a lever, and wherein each jaw has a compression surface having an area. The apparatus also includes a compressing mechanism configured to move each lever in a non-linear motion such that the area of a compression surface exposed to the material decreases with the inward movement of that compression surface; and a plurality of shaping elements projecting from at least one compression surface, wherein the plurality of shaping elements is configured to impart a pattern in the material.

In another aspect, the present disclosure provides an apparatus for compressing a material, the apparatus having a central longitudinal axis and including a plurality of levers and a plurality of jaws, wherein each jaw is attached to a lever, and wherein each jaw has a compression surface having an area. The apparatus also includes a compressing mechanism configured to move each lever in a non-linear motion such that the area of a compression surface exposed to the material decreases with the inward movement of that compression surface; and a plurality of shaping elements each projecting from a compression surface, wherein the plurality of shaping elements is configured to impart a plurality of grooves in the material.

BRIEF DESCRIPTION OF THE DRAWINGS

The foregoing and other features and aspects of the present disclosure and the manner of attaining them will become more apparent, and the disclosure itself will be better understood by reference to the following description, appended claims and accompanying drawings, where:

Figure 1:
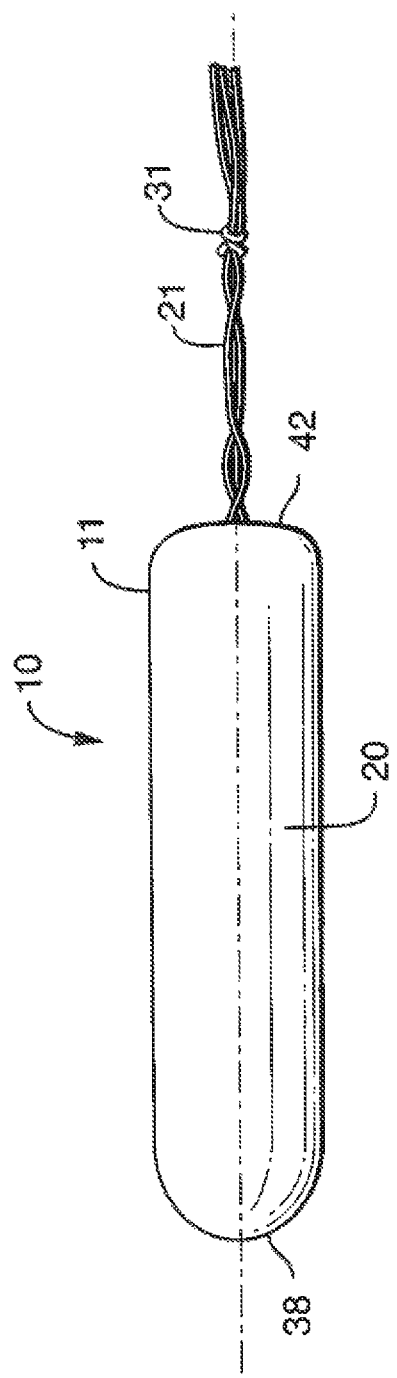
FIG. 1 representatively illustrates an exemplary tampon of the present disclosure.

Repeat use of reference characters in the present specification and drawings is intended to represent the same or analogous features or elements of the present disclosure. The drawings are representational and are not necessarily drawn to scale. Certain proportions thereof might be exaggerated, while others might be minimized.

DETAILED DESCRIPTION

Prior presses have a multiplicity of compression members commonly called jaws that contact the outer surface of the uncompressed material and simultaneously reduce the material diameter until sufficient densification of the fibers occurs such that the pressure created temporarily deforms the materials into a stable, pressed condition.

Prior presses with multiple compression jaws operate in a motion that is generally in a linear, radial direction (in and out) from the theoretical center of the press. As such, the multiple independent jaws have spaces between adjacent jaws where the materials near the surface of the uncompressed material will become deformed during the compression process. Portions of the uncompressed material can migrate around the compression surface of the jaw and into the spaces between adjacent jaws thus becoming caught between the jaws at minimum compression. Such deformation can intentionally or unintentionally create undulations or wrinkles to accommodate the reduction of diameter during the compression process. In some applications this is a desirable effect to create more uniform densities or to enhance the surface area of a product. In other applications, such as those described herein, the deformation can cause wrinkles or a line of weakness such that at least a portion of a product is damaged or substantially compromised in strength. The uncompressed material can have the additional propensity to undesirably migrate into the spaces between jaws.

A specific but non-limiting example of the use of the press of the present disclosure is in the manufacture of tampons. The tampon of the present disclosure is designed to be inserted above the introital region of a woman's vagina and is designed to function so as to intercept the fluid flow of menses, blood, and other body fluids and prevent the fluid from exiting the vagina. While the pledgets of the present disclosure are described for use as a menstrual device, it will be readily apparent that the pledgets can also be used as any other suitable vaginal insert, such as a pessary. Likewise, while the pledgets of the present disclosure are generally described as being absorbent, it will be readily apparent that the pledgets can be coated or otherwise treated to be partially or completely non-absorbent.

Improvement to the effectiveness of a tampon product can be made by adding a secondary absorbent layer to the absorbent structure of the tampon. The secondary layer has individual contact members that can increase the mucosal contact region with the vaginal wall beyond the diameter of the standard radially-wound tampon. Although this feature is advantageous for its ability to contact and absorb vaginal fluids over a larger surface area, the contact member or petal can become bent, twisted, or torn during the tampon-making process, resulting in the petal not lying flat to the outer surface of the tampon soft roll/uncompressed blank and/or to the compressed tampon pledget during the compression process.

It should be noted that the press device described herein is described using tampon compression as an example, but is equally suitable for use in compressing any compressible material including raw materials and products, and particularly any generally uncompressed material that can be made into a compressed cylindrical material.

As is shown in FIG. 1, exemplary tampons 10 include a mass of fibrous material 11 compressed into a generally cylindrically-shaped pledget 20. The tampon 10 generally has an insertion end 38 and an opposite withdrawal end 42. The insertion end 38 is designed to be the first part of the tampon that enters the woman's vaginal cavity. In some aspects, the insertion end 38 can be rounded or otherwise shaped to facilitate insertion. While in use, the pledget 20 of the present disclosure is designed to be positioned entirely within the woman's vagina. The tampon 10 can also include contact elements (not shown) such as those described in co-pending U.S. patent application Ser. Nos. 13/333150, 13/333311, 13/537138, and 13/537153, which are incorporated herein to the extent they do not conflict herewith.

The tampon 10 further includes a withdrawal string 21 for assisting in removing the tampon 10 from the woman's vagina. The withdrawal string 21 can be attached to the pledget 20 in any suitable manner. The withdrawal string 21 can further include one or more knots 31 to prevent fraying of the withdrawal string 21 and to provide a point where a woman can grasp the withdrawal string 21 when she is ready to remove the tampon 10 from her vagina.

When the woman pulls on the withdrawal string 21, forces are applied to the connection points between the withdrawal string 21 and the pledget 20. These forces are counteracted by the frictional forces between the pledget 20 and the vaginal walls. The frictional forces vary depending upon the saturation level of the pledget, the presence and/or type of cover material, pledget expansion, pledget orientation, the rheology of the body fluids present, and numerous other factors. Regardless of the various factors, it is desirable that the integrity of the pledget 20 be such that it can withstand the countervailing forces without delaminating, unrolling, unfolding, telescoping, or otherwise structurally degrading. While not wishing to be bound by theory, it is believed that these and other structural degradations are caused, at least in part, by shifting between various layers or structures of the pledget 20. These shifts are believed to be compounded by the fact that the pledgets 20 are generally made from ribbons of fiber that can be wound, folded, stacked, gathered, bunched, waded, bagged, or the like. Past efforts to stabilize the pledget 20 have included the use of binder fibers, adhesives, grooved compression, needling, microwave radiation, and the like in an effort to achieve fiber-to-fiber stability. While these methods have had mixed success, the present disclosure is believed to increase layer or structure integration by mechanically driving uniform compression and limiting pinch points.

The apparatus described herein is designed to radially compress a material, including the specific example of manufacturing a tampon 10. The apparatus has compressing surfaces and a compressing mechanism to move the compressing surfaces in a nonlinear motion while compressing the material. As the apparatus compresses, the compressing surface area decreases and circumferential gapping is maintained close to zero over the relevant range of the apparatus. The operating range of the apparatus is defined as the range between the maximum compression diameter and the minimum compression diameter. The ratio of the initial compression diameter to the final compression diameter, or the compression ratio, obtainable with this apparatus is one or greater in one aspect, greater than two in another aspect, and greater than three, four, five, six, seven, eight, nine, ten, 15, 20, or more in other aspects. The initial compression diameter is the effective diameter of the material prior to compression, which is essentially the minimum diameter to which the apparatus must be opened to accept the material. The diameter in the preceding terms is the diameter of the hypothetical cylinder 110 defined below. The final compression diameter is the desired diameter of the material after compression.

By maintaining circumferential gapping essentially at zero over the relevant range of the apparatus, the compression jaws can reinforce each other to improve apparatus stability.

Figure 2:
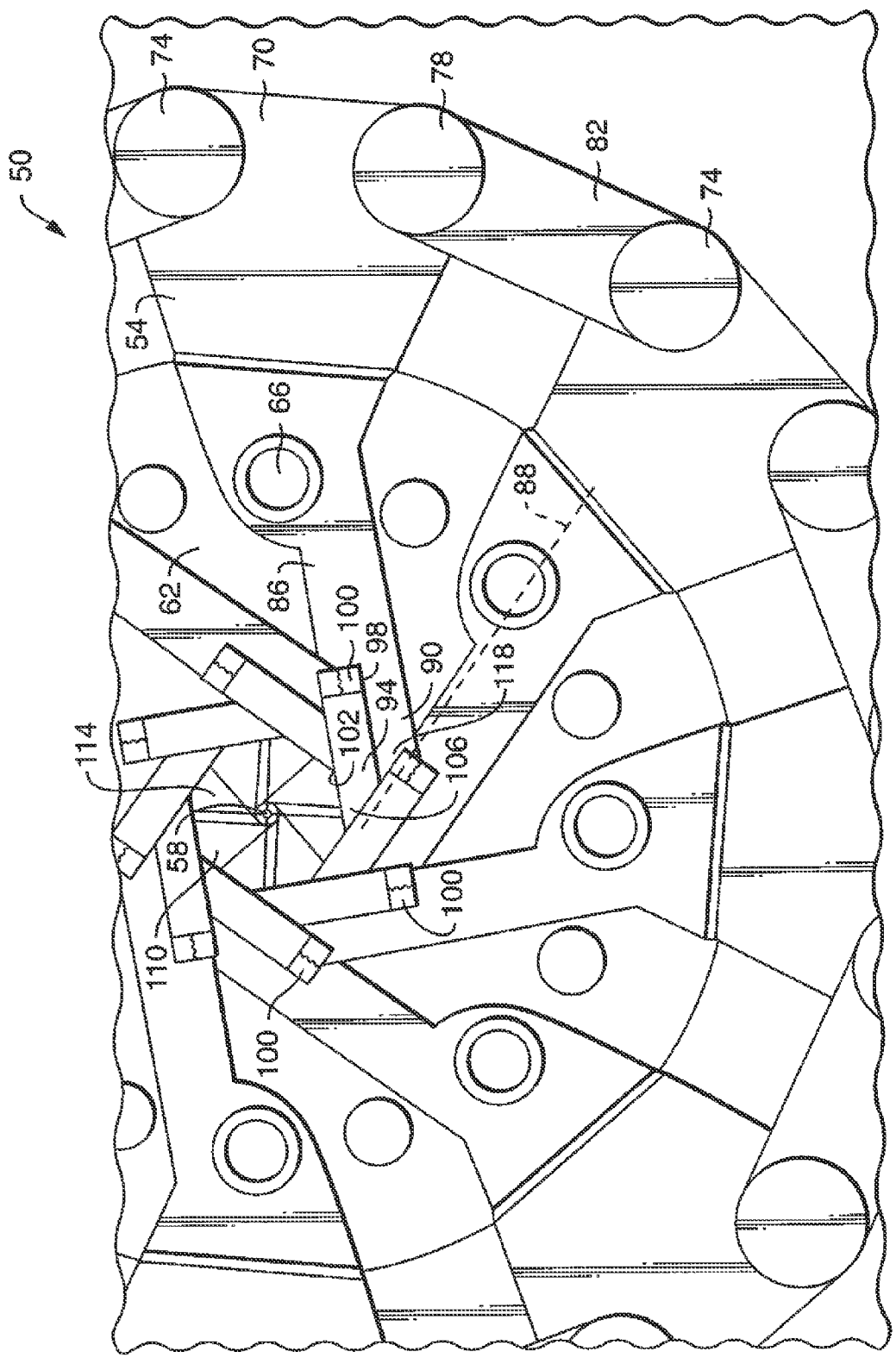
FIG. 2 representatively illustrates an exemplary apparatus used in making the tampon of FIG. 1, in an open position.
Figure 3:
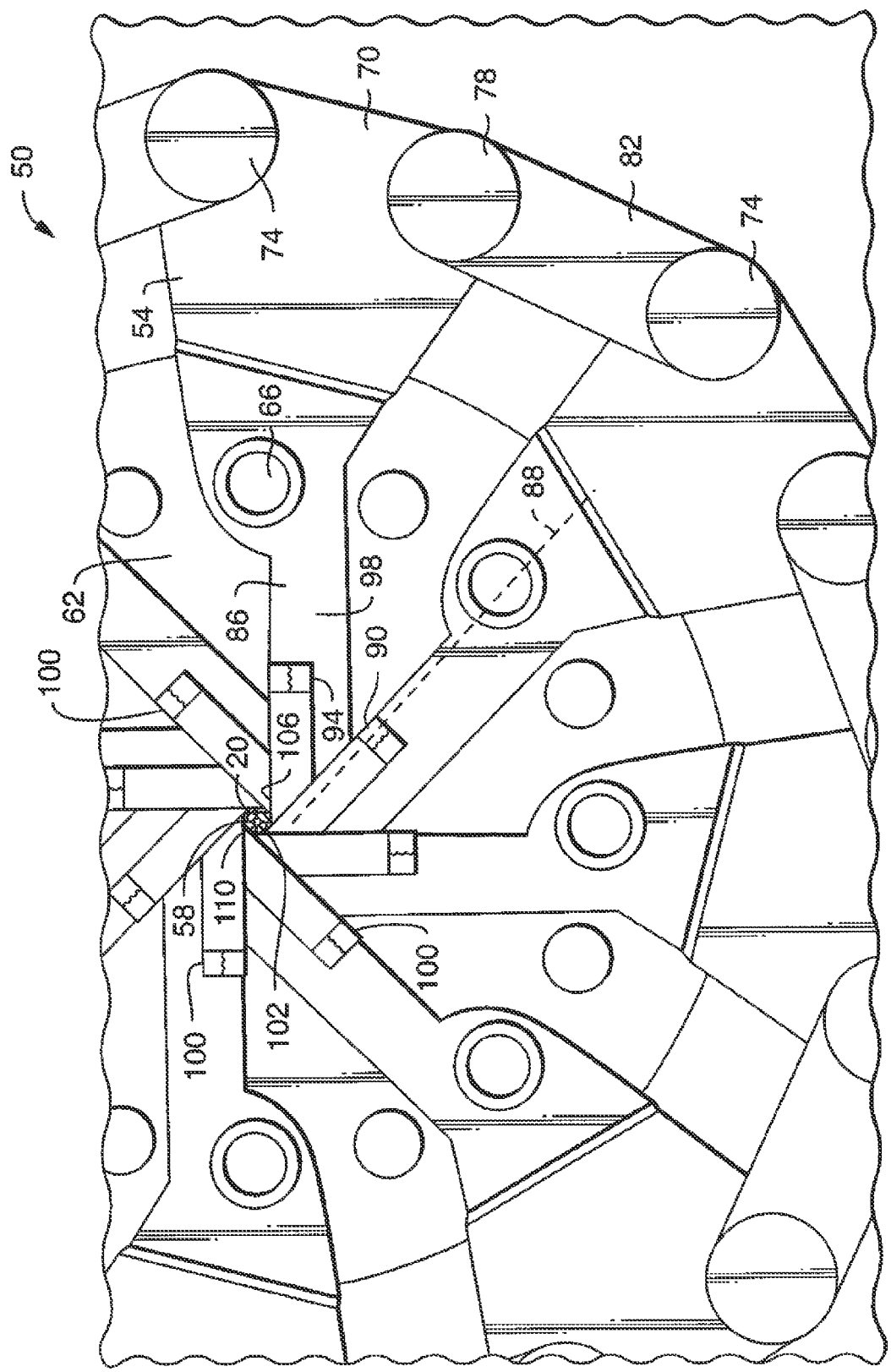
FIG. 3 representatively illustrates an exemplary apparatus used in making the tampon of FIG. 1, in a minimum compression position.
Figure 4:
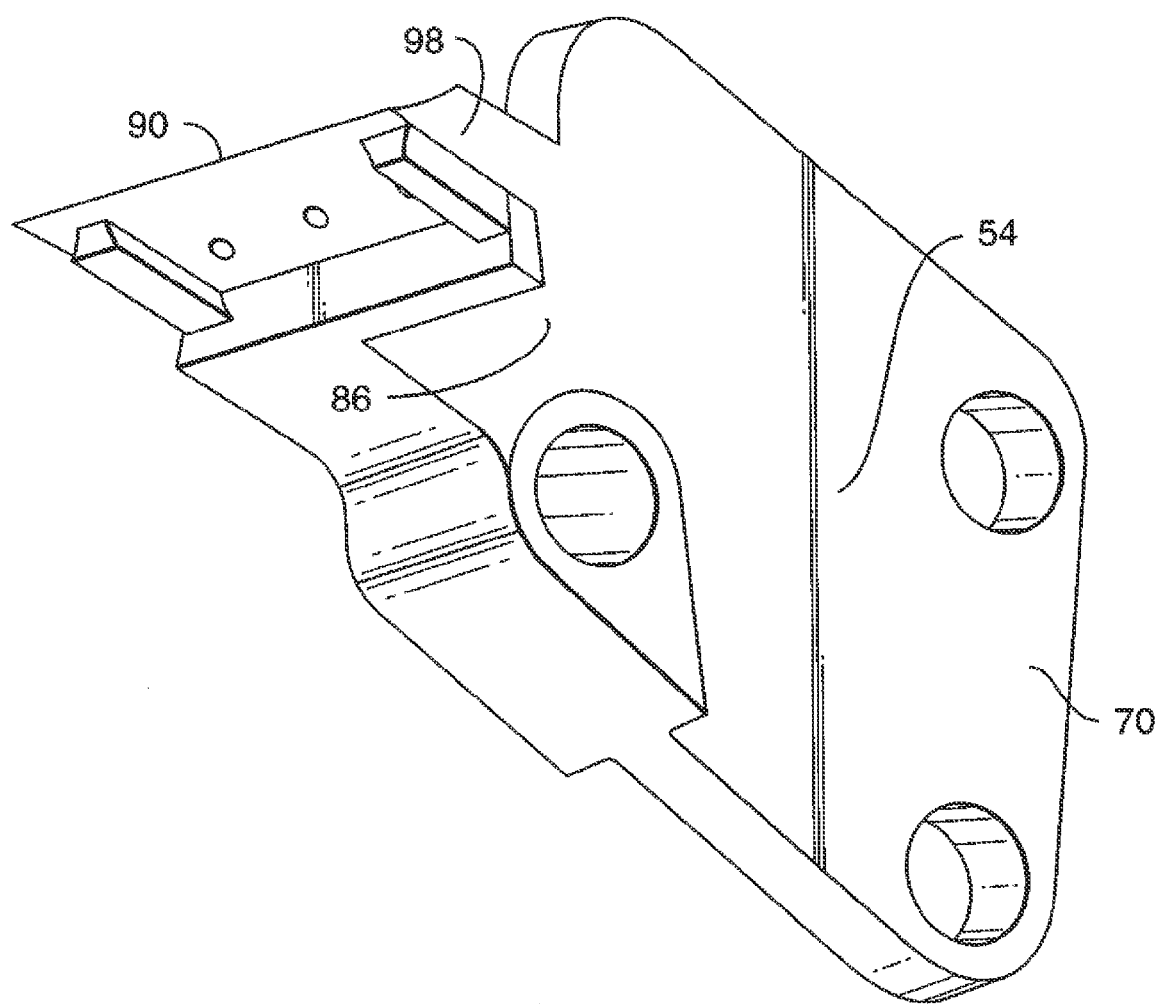
FIG. 4 representatively illustrates a lever used in the apparatus of FIGS. 2 and 3.

A press device 50 for manufacturing the tampon 10 described herein is illustrated in FIG. 2. The press device 50 used as an example here includes eight levers 54 (see FIGS. 2-4), although any suitable number of levers 54 can be accommodated. The center of the press device 50 defines a central longitudinal axis 58, which is the point at which the jaws 94 meet when the levers 54 and jaws 94 are at their innermost extent of travel. Each lever 54 is connected to a fixed ring 62 with a pivot pin 66 and is pivotable within certain limits about the pivot pin 66. Each lever 54 has a lever outer end 70 that is pivotably linked by first and second coupling pins 74, 78 to adjacent chain links 82 as a part of a drive mechanism (not shown). The first and second coupling pins 74, 78 and the pivot pins 66 can each be positioned in generally circular array, or in any other suitable array. The spacing between adjacent coupling pins 74, 78 and between adjacent pivot pins 66 is determined by the number of levers 54 to be included within the circle.

The levers 54 are designed as angle levers and each includes a lever arm 86 that is positioned radially inwardly. Each lever 54 has a lever longitudinal axis 88 extending from the lever outer end 70 through the pivot pin 66 to a radially-inward end portion 90 of each lever arm 86. The radially-inward end portion 90 includes a jaw 94 used in compression. The jaw 94 can be formed integrally with the lever arm 86 and therefore be a portion of the lever 54 itself, the jaw 94 can be attached to the lever arm 86 at a tool carrier 98 on the radially-inward end portion 90 of the lever arm 86, or the jaw 94 can be associated with the lever 54 in any suitable manner. In various aspects of the present disclosure, the number of levers and jaws can be 3, 4, 5, 6, 8, 10, 12, 16, or any other suitable number.

Figure 5:
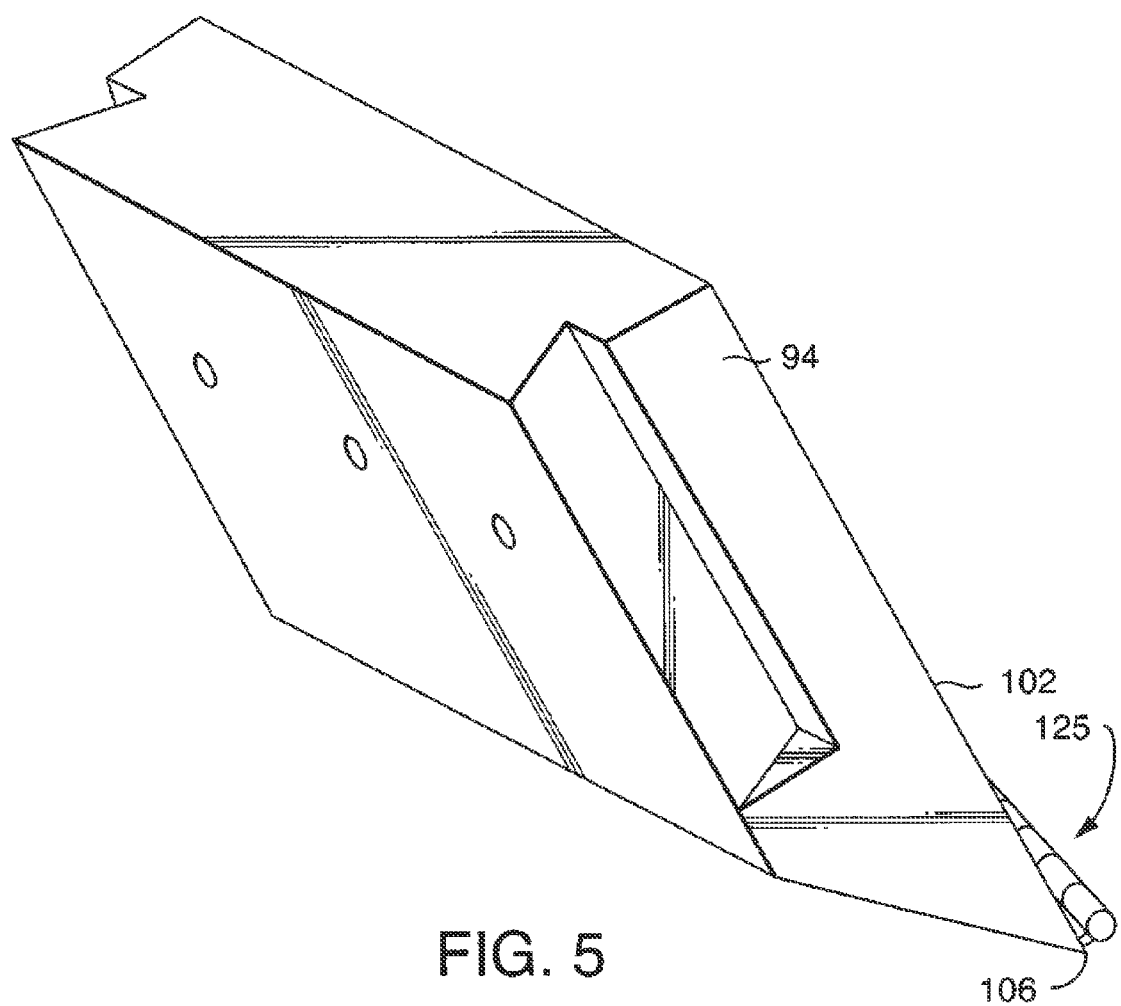
FIG. 5 representatively illustrates a jaw used in the apparatus of FIGS. 2 and 3.

Each jaw 94 includes a compression surface 102 and a jaw edge 106 (see FIG. 5). The compression surface 102 defines a plane that is generally parallel to the lever longitudinal axis 88. In the illustrated aspect, each jaw 94 projects toward an adjacent jaw 94 where the adjacent jaw 94 is positioned in a clockwise direction from the first jaw 94. The jaw edge 106 of one jaw 94 is disposed in the vicinity of the compression surface 102 of the clockwise-adjacent jaw 94. The topography of a given jaw edge 106 essentially matches the topography of the compression surface 102 of an adjacent jaw 94. The press device 50 is arranged such that a plane defined by the compression surface 102 of each jaw 94 is at all points in the compression cycle tangential to the central longitudinal axis 58.

In addition, each compression surface 102 defines an area that is exposed to the material to be compressed. This area is generally between the jaw edge 106 of a particular jaw 94 and the line or point on that jaw 94 that is contacted by or adjacent to the jaw edge 106 of an adjacent jaw 94. For example, in a press device 50 with eight jaws 94 cooperate to form a generally octagonal compression cavity. One side of that octagon defines the area of a compression surface 102 exposed to the material to be compressed. As the jaws 94 move inwardly, the octagon shrinks, and the area of each side and therefore each compression surface 102 decreases. The compression surfaces 102 define a hypothetical cylinder 110 that is, in a radial direction, a hypothetical circle of maximum diameter that can be inscribed within the compression surfaces 102. In the example described in this paragraph, the circle is a circle of maximum diameter that is inscribed within the octagon defined by the compression surfaces 102. As a result, as the jaws 94 move inwardly, the hypothetical cylinder 110 also shrinks in diameter.

The attachment of the jaw 94 to the tool carrier 98 can include a biasing mechanism 100 configured to urge the jaw 94 in a direction away from the pivot pin 66 and toward a clockwise-adjacent jaw 94. In other words, the biasing mechanism 100 pushes the jaw 94 toward a clockwise-adjacent jaw 94, whereas such clockwise-adjacent jaw 94 resists such pushing. In this manner, any gap that would otherwise exist between adjacent jaws 94 will be closed by the contact between adjacent jaws 94.

The biasing mechanism 100 can be any suitable mechanism, component, force, or combination of these capable of biasing a jaw 94 toward an adjacent jaw 94. The biasing mechanism 100 can be disposed on one or more of a lever 54, jaw 94, and any other element of the press device 50. The biasing mechanism 100 can be disposed between a lever 54 and a jaw 94, particularly on, in, or in the vicinity of a tool carrier 98. Suitable biasing mechanisms 100 include, but are not limited to, bevel, tension, and compression springs; pneumatic and/or hydraulic components including cylinders or bladders; elastomeric components such as an elastomeric block or an elastomeric band; mechanical gearing such as a rack and pinion or non-circular gearing; a cam mechanism including followers or a contoured wedge mechanism; electrical components including a solenoid; magnetic forces; vacuum; mechanical engagement such as a t-slot pin-type mechanism; a supplemental linkage connected between two or more jaws 94, and any combination of these. The biasing mechanism 100 can be disposed directly on or near the jaws 94, or can be external components that direct influence to the jaws 94.

Activating the drive mechanism and rotating the chain link 82 causes the lever 54 to pivot about the pivot pin 66. The lever 54 pivots such that the radially-inward end portion 90 of the lever arm 86 moves radially inward when the chain link 82 is rotated in a clockwise direction in this example. Each compression surface 102 moves radially inwardly with the end portion 90 to which it is attached. Thus, the press device 50 closes when the chain link 82 is rotated in a clockwise direction in this example, and the press device 50 opens when the chain link 82 is rotated in a counterclockwise direction in this example. It can be seen that the jaws 94, and particularly a point on a jaw 94, can be configured to move in a non-linear manner, or in a curvilinear manner depending on the arrangement of levers, pins, fixed rings, and chain links.

In many prior presses, linear or quasi-linear travel of the jaws in a radial direction leaves a gap between jaws in which portions of the uncompressed material can be trapped. In some cases where a multi-lobed tampon is desired, such intrusion of uncompressed material into a gap is intentional. Other prior presses seek to address the gap issue by installing a second set of jaws in the gaps between the first set of jaws. This second set of jaws is intended to at least partially fill the gaps to address the portion of uncompressed material intruding in the gaps. The two sets of jaws leads to a complicated arrangement of jaws and levers.

In addition, in many prior presses, jaws can interfere with and impinge upon adjacent jaws at small compressions (i.e., when the jaws near their inward extent of travel). In contrast, the press device 50 of the present disclosure can theoretically move inwardly until the jaw edge 106 of each jaw 94 meets the others at the central longitudinal axis 58 of the press device 50. In other words, the jaws 94 can move inwardly until the hypothetical cylinder 110 defined by the compression surfaces 102 reaches a diameter of zero.

FIG. 2 illustrates that in the open starting position the jaw edges 106 of the jaws 94 are not directed toward the central longitudinal axis 58 of the press device 50 but tangentially toward a hypothetical cylinder 110 that surrounds the central longitudinal axis 58 at a selected distance. Thus it is achieved that the compression forces that are applied by the jaws 94 are not centrally but tangentially directed toward a circle that surrounds the material to be manufactured at a selected distance.

In the open starting position of the device 50 according to FIG. 2, a blank 114 of material is inserted into the opening between the compression surfaces 102. This blank 114 in one aspect is manufactured by winding up an absorbent material section. By rotating the chain links 82 clockwise relative to the fixed ring 62, the compression surfaces 102 are first brought into an intermediate position and finally into the end position illustrated in FIG. 3. With this pivoting movement, the levers 54 are pivoted about the pivot pins 66. A comparison of FIG. 3 with FIG. 2 shows that during this movement the deformation forces that are applied by the compression surfaces 102 lead to a volume reduction of the blank 114 that is uniform about the periphery and transform the blank 114 into a compressed blank 114 (or a pledget 20 in the case of a tampon 10). After slightly opening the jaws 94, the compressed blank 114 is removed from the device 50.

Prior presses incorporate multiple compression jaws that cooperate with each other such that the clearance between adjacent jaws forms a gap. Each gap defines a gap centerline. Lines including the gap centerlines of prior presses generally pass through or near the center of such presses. This arrangement in prior presses allows material to intrude into the gap. In the press device 50 of the present disclosure, the elimination of gaps helps prevent intrusion of material into a gap.

In various aspects of the present disclosure, the substantially reduced clearance between adjacent jaws 94 approaches zero such that there is no practical gap present throughout the compression cycle, such that migration of material around the contacting surfaces is substantially limited.

Prior devices tend to teach the need for a highly complex devices where the die cavity is operative only by the incorporation of a number of members including stationary members, spring-loaded members, and multiple forming fingers. These devices also can require an outer ring in combination with a cam mechanism, motor, and oscillating gear box to drive the members back and forth to compress and open a cavity.

The present disclosure advantageously provides a simple one jaw (finger) member 94 that is mounted to a movable lever 54 that rotates or pivots about a pivot pin 66 to move each jaw 94 in an arcuate motion to create a generally continuous compression cavity. The press device 50 does not require a ball bearing or roller bearing as in prior devices. Instead a simple bearing surface is all that is needed. There is also no need in the present disclosure for a stationary member to form a portion of the compression cavity described.

Prior devices require at least two different members to form a compression cavity, whereas the present disclosure advantageously teaches that only one member is necessary. Prior devices also require a complex mechanism with various linkages to open and close the press. The present disclosure advantageously provides a single set, in one example, of eight jaws 94 with their corresponding levers 54 to form the compression cavity.

The present disclosure recognizes that, although a continuous compression cavity is one means to accomplish uniform compression, uniform compression can also be accomplished with a tangential space present between adjacent jaws 94, because the compression surface 102 also creates uniform pressure, as in the present disclosure. Although the tangential space in one aspect of the present disclosure has a discrete step at the interface where one jaw 94 overlaps an adjacent jaw 94, the surface segments that create pressure are continuous throughout the compression cavity when viewed from a perspective view in the radial direction.

It should be noted that prior devices do not teach or recognize any adverse consequences to having spaces between adjacent jaws due to the general radial orientation of the compression jaws. In fact, many such presses require a gap between compression surfaces to allow for the creation of radially-projecting lobes on a tampon body.

An advantage over existing radially-oriented jaw presses is that the profile of the radial gap created between jaws 94 is essentially eliminated.

A further advantage of the present disclosure over existing presses is that complexity, cost, maintainability, press open dimensional range, and flexibility of the press device 50 are greatly simplified such that now each jaw 94 functions as a compression surface 102 and forms a segment of the compression cavity. This advantageously allows each jaw 94 to be optimized for various features because of the inter-changeability of jaws 94. The prior art shows that a holder and/or a stationary surface in combination with the jaw (finger) 94 is required to form at least a portion of the compression cavity. At minimum compression, adjacent jaws 94 of the present disclosure also advantageously cooperate with each other to provide additional resistance to the high pressures created at the surface of the adjacent jaw 94 that is in front of it.

An additional advantage of the present disclosure is the ability of the arrangement described to be used in conjunction with standard and existing tampons or other machinery. This results in minimized equipment development time and costs.

In further aspects of the present disclosure, the press device 50 can be used to make a tampon 10 or other compressed product having increased layer or structure integration. The addition of one or more shaping elements 125 to the press device 50 can be used to impart indentations, grooves, bulges, and any other suitable topographical elements to the material. Various examples are illustrated together in FIG. 6; the material of the present disclosure can include one or more of the illustrated features in any combination.

Figure 6:
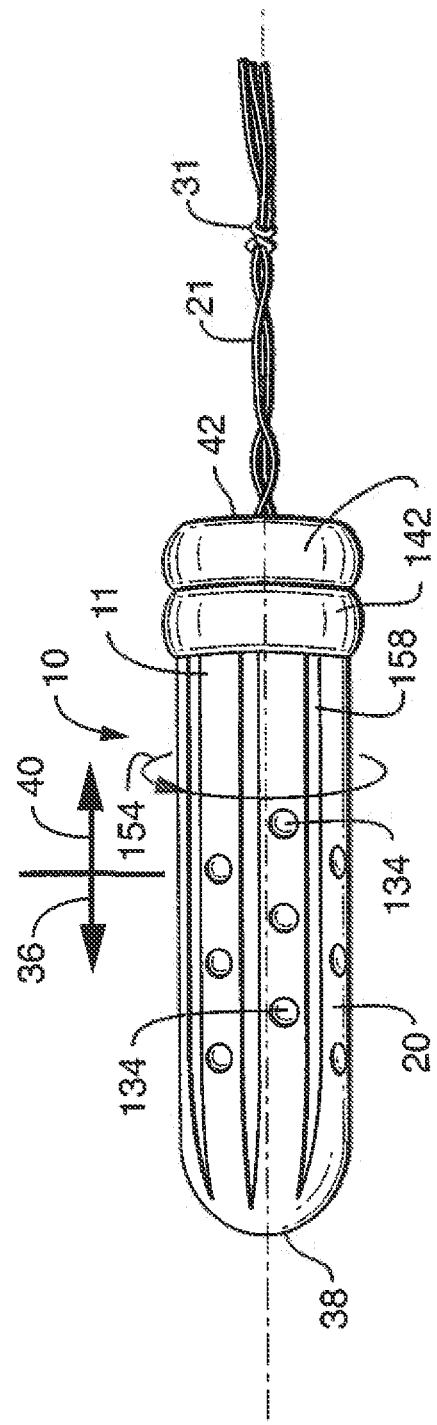
FIG. 6 representatively illustrates an exemplary tampon of the present disclosure.
Figure 7:
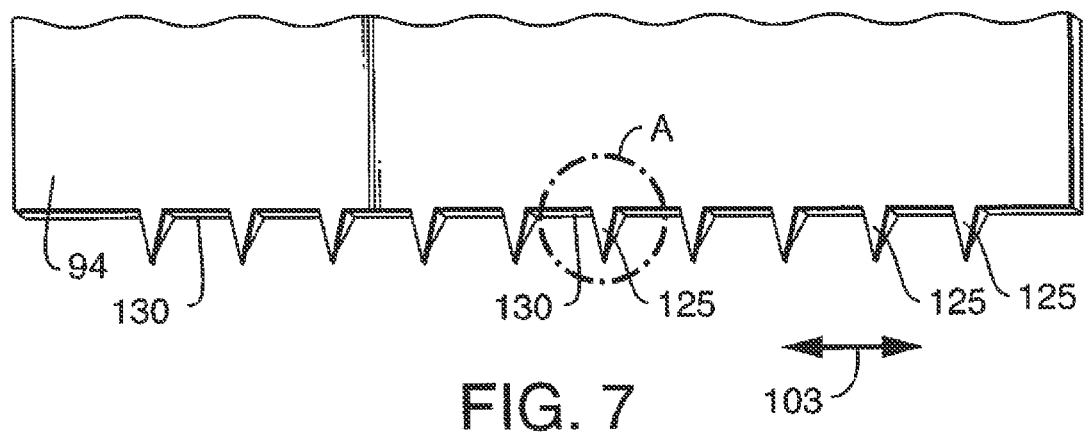
FIG. 7 representatively illustrates a cross-section view of an exemplary jaw with shaping elements of the present disclosure.
Figure 8:
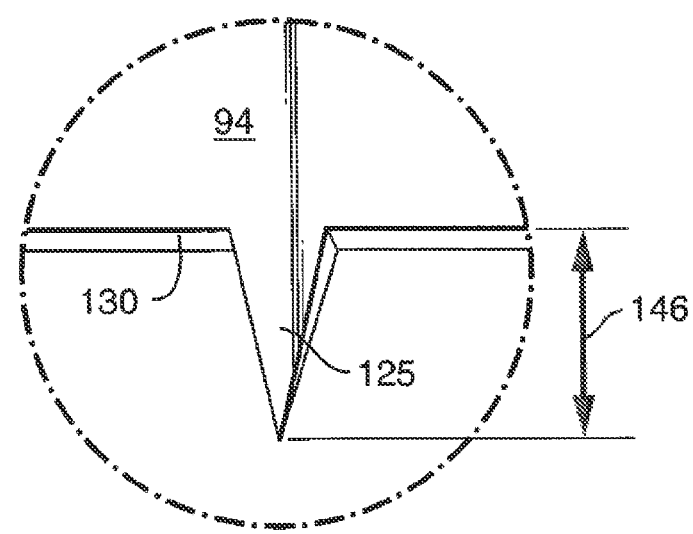
FIG. 8 representatively illustrates an enlarged view of detail A of FIG. 7.
Figure 9:
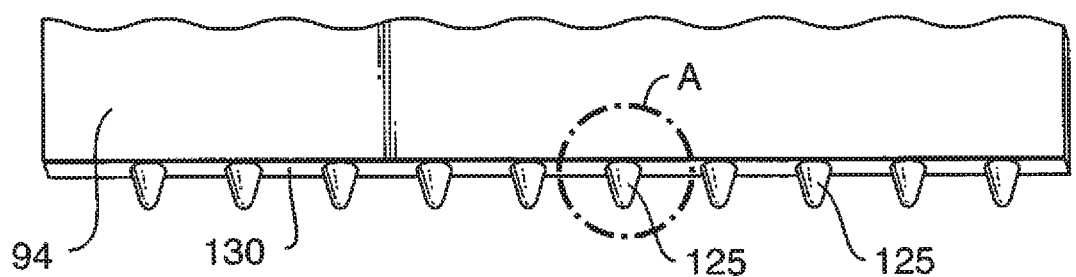
FIG. 9 representatively illustrates a cross-section view of another exemplary jaw with shaping elements of the present disclosure.
Figure 10:
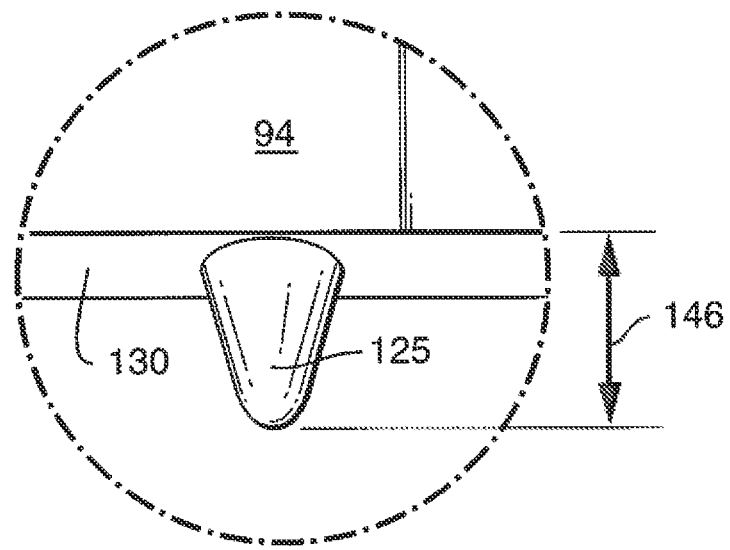
FIG. 10 representatively illustrates an enlarged view of detail A of FIG. 9.
Figure 11:
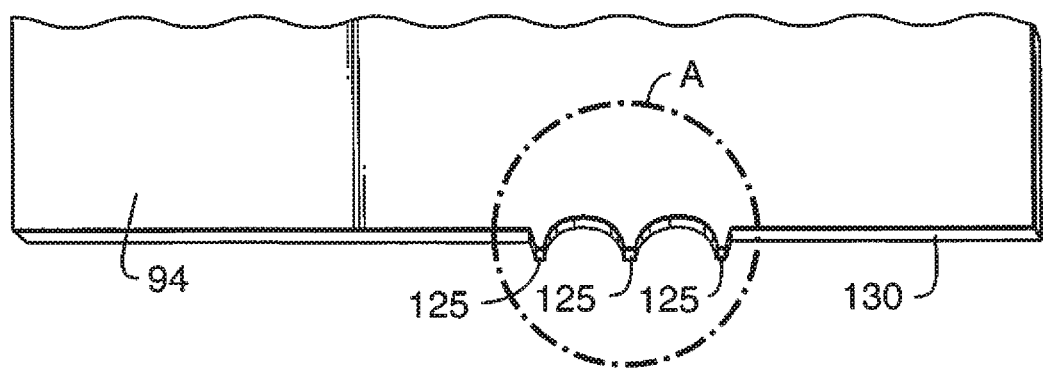
FIG. 11 representatively illustrates a cross-section view of another exemplary jaw with shaping elements of the present disclosure.
Figure 12:
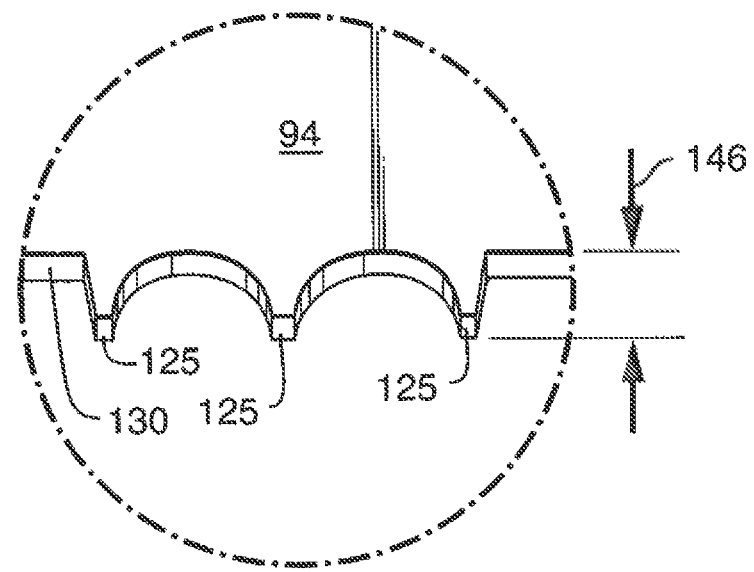
FIG. 12 representatively illustrates an enlarged view of detail A of FIG. 11.

FIG. 5 illustrates a perspective view of a jaw 94 having a shaping element 125. FIGS. 7-17 illustrate various cross-sectional views of exemplary jaws 94 having profiling surfaces 130 and shaping elements 125 extending therefrom. The profiling surfaces 130 are adapted to compress the cylindrical blank 114 and provide shape to a portion of the outer surface of the resultant pledget 20. Likewise, the shaping elements 125 are adapted to compress the cylindrical blank 114 and then penetrate the pledget 20 to form the discrete indentations 134 (FIG. 6) that are believed to integrate the absorbent layers or structure proximate the point of penetration. The point of penetration results in an indentation 134 (FIG. 6).

In various aspects, the shaping elements 125 can have any suitable shape, dimensions, and/or volume. In some aspects, the shaping elements 125 can be in the shape of a pyramid, a cone, a cylinder, a cube, an obelisk, or the like, or any combination thereof. The shaping elements 125 can have a cross section that is bulbous, rectilinear, trapezoidal, polygonal, triangular, any other suitable shape, or any combination thereof. The shaping element 125 can be in the form of a pin that is one of cylindrical, conical, elliptical, and any other suitable shape. The shaping element 125 need not be circumferentially symmetric; the shaping element 125 can be elongate and extend partially or entirely across the area of the compression surface 102 (see FIG. 5). In various aspects, the shaping element 125 can have an orientation with respect to the apparatus central longitudinal axis 58 that is generally parallel, perpendicular, angled, or a combination of these. In various other aspects, the shaping element 125 can be a cavity in the compression surface 102 or a curvilinear surface on the compression surface 102.

Figure 15:
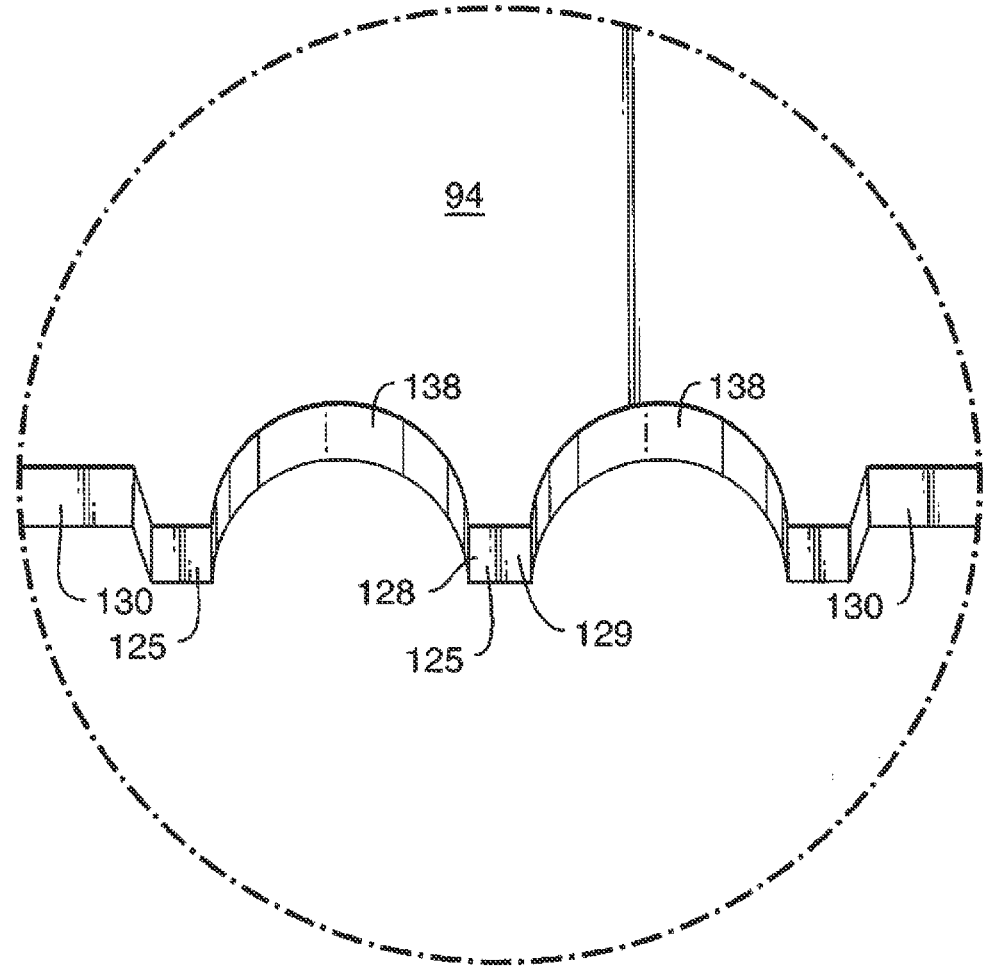
FIG. 15 representatively illustrates an enlarged view of detail B of FIG. 13.
Figure 16:
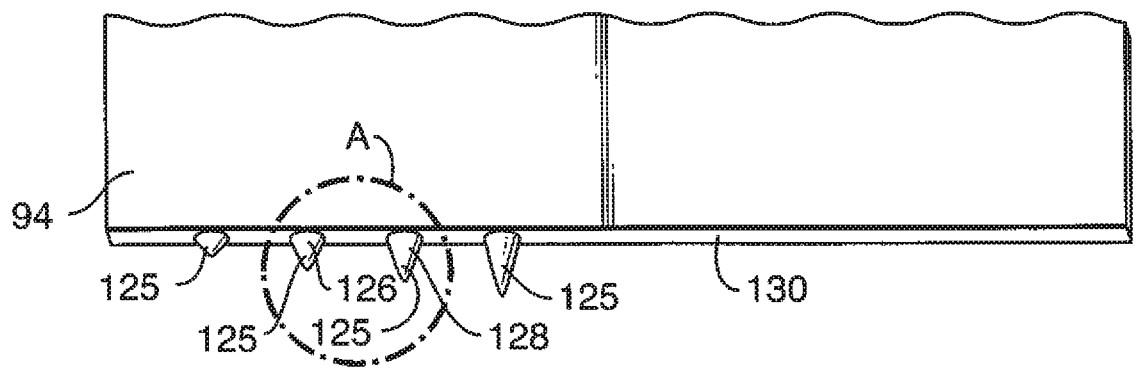
FIG. 16 representatively illustrates a cross-section view of another exemplary jaw with shaping elements of the present disclosure.
Figure 17:
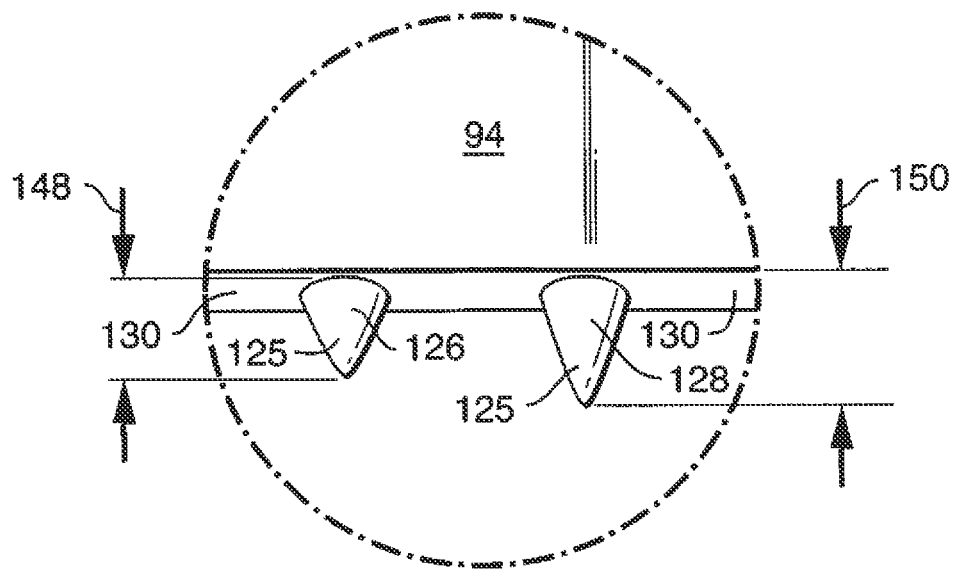
FIG. 17 representatively illustrates an enlarged view of detail A of FIG. 16.

For example, the shaping elements 125 can be in the shape of a cone with a relatively pointed such as that illustrated in FIGS. 16 and 17. In another example, the shaping elements 125 can be in the shape of a cone with a rounded such as that illustrated in FIGS. 9 and 10. In some aspects, the shaping elements 125 can be in the shape of a pyramid such as those illustrated in FIGS. 7 and 8. In some aspects, the shaping elements 125 can have a rectangular shape at the apex with at least one curving side such as those illustrated in FIGS. 11, 12, 13, and 15.

Figure 13:
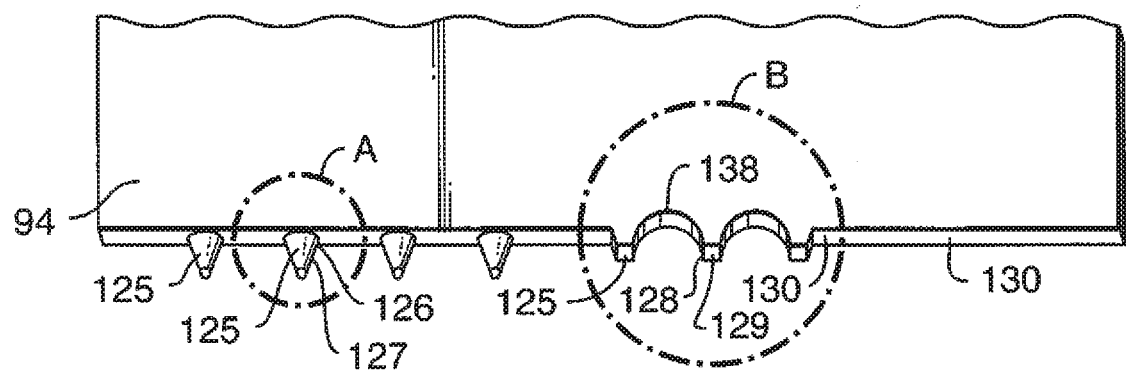
FIG. 13 representatively illustrates a cross-section view of another exemplary jaw with shaping elements of the present disclosure.
Figure 14:
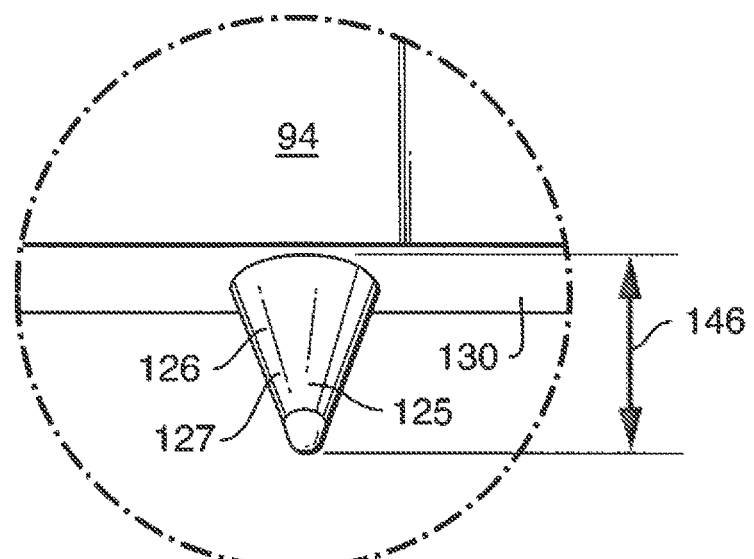
FIG. 14 representatively illustrates an enlarged view of detail A of FIG. 13.

In some aspects, the jaws 94 can have shaping elements 125 in the form of a discrete relief 138 such as those illustrated in FIGS. 13 and 15. The discrete relief 138 extends into the jaw 94 and can have any suitable shape. For example, as illustrated in FIG. 15, the discrete relief 138 can have an arched shape. In these aspects, when a plurality of jaws 94 compress the cylindrical blank 114 into the pledget 20, a circumferentially raised ring 142 is formed as illustrated in FIG. 6.

In various aspects, one or more of the jaws 94 can include a first shaping element 126 having a first shape 127 and a second shaping element 128 having a second shape 129 that is different than the first shape 127. For example, FIG. 13 representatively illustrates a first shaping element 126 having a first shape 127 wherein the first shape 127 is a cone (FIG. 18). FIG. 17 also representatively illustrates a second shaping element 128 having a second shape 129, wherein the second shape 129 is more cubic.

In some aspects, a press device 50 can include a first jaw 94 having a first shaping element 126 having a first shape 127, and a second jaw 94 having a second shaping element 128 having a second shape 129. In various aspects, the first shape 127 and the second shape 129 can be the same or can be different. For example, in some aspects, the first jaw 94 can include first shaping elements 126 having the shape of cones and the second jaw 94 can include second shaping elements 128 having the shape of pyramids.

In various aspects, the shaping elements 125 can extend any suitable distance from the profiling surface 130. For example, referring now to FIGS. 8, 10, 12, and 14, the shaping elements 125 can have an extension dimension 146 of at least 0.5 mm, at least 1 mm, at least 1.5 mm, at least 2 mm, at least 2.5 mm, or at least 3 mm. In various aspects, one or more jaws 94 can have shaping elements 125 wherein two or more of the shaping elements 125 have the same extension dimension 146 such as those illustrated in FIGS. 7 and 9. In some aspects, one or more jaws 94 can have two or more shaping elements 125 having different extension dimensions 146 such as those illustrated in FIG. 16. Specifically, FIG. 16 illustrates a jaw 94 having a profiling surface 130 wherein a first shaping element 126 has a first extension dimension 148 (FIG. 17) and a second shaping element 128 has a second extension dimension 150 (FIG. 17). As illustrated, the second extension dimension 150 is greater than the first extension dimension 148.

In some aspects, a press device 50 can include a first jaw 94 having a first shaping element 126 having a first extension dimension 148. Likewise, the press device 50 can include a second jaw 94 having a second shaping element 128 having a second extension dimension 150. In various aspects, the first extension dimension 148 and the second extension dimension 150 can be the same or can be different. For example, in some aspects, the first jaw 94 can include shaping elements 125 having an extension dimension 146 that is less than the extension dimension 146 of the shaping elements 125 of the second jaw 94.

Because the profiling surfaces 130 of the jaws 94 define the compressed diameter of the pledget 20, the extension dimension 146 equals the penetration depth of the shaping element 125 into the pledget 20. The penetration depth can be defined as a percentage of the compressed diameter of the pledget 20. For example, in various aspects, the shaping elements 125 can have a penetration depth of at least 20%, at least 30%, at least 40%, or at least 50% of the compressed diameter of the pledget 20. For example, in other aspects, the compressed diameter can be about 6.6 mm and the extension dimension 146 can be about 2.55 mm such that the penetration depth is 39% of the compressed diameter.

In various aspects, the shaping elements 125 can have a volume of at least 3, at least 4, or at least 5 cubic millimeters. In specific aspects, the shaping elements 125 can be blunted cones having a base diameter of 2.523 mm and a height of 2.546 mm for a volume of 5.045 cubic millimeters. In various aspects, the volume and/or the shape of the shaping elements 125 can be selected to provide the desired layer integration. In various aspects, at least 80%, at least 90%, or at least 95%, or 100% of the volume of the shaping elements 125 can penetrate the compressed pledget 20. Thus, in these aspects, the displaced volume of absorbent material that initially forms the discrete indentations 134 is at least 80%, at least 90%, at least 95%, or 100% of the volume of the shaping elements 125.

The pledget 20 defines a first half 36 having an insertion end 38 and a second half 40 having a withdrawal end 42. In some aspects, the methods of the present disclosure include penetrating the pledget 20 with shaping elements 125 such that there are more discrete indentations 134 formed in the first half 36 than in the second half 40. This is believed to be beneficial because the withdrawal string 21 is frequently anchored in the first half 36 of the pledget 20 while extending from the withdrawal end 42 of the second half 40. As such, the withdrawal forces applied are first directed at the first half 36. Thus, creating greater layer integration via the discrete indentations 134 in the first half 36 is believed to counteract the withdrawal forces and help maintain the integrity of the pledget 20. In some aspects, the first half 36 has at least 25%, at least 50%, or at least 75% more discrete indentations 134 than the second half 40. In some aspects, all the discrete indentations 134 can be in the first half 36. In some aspects, at least 60%, at least 70%, at least 80%, or at least 90% of the discrete indentations 134 can be in the first half 36.

In some aspects, the apparatus of the present disclosure can be used to form one or more raised circumferential rings 142 around the pledget 20 as illustrated in FIG. 6.

In some aspects, the apparatus of the present disclosure can be used to penetrate the pledget 20 to form one or more longitudinal rows of discrete indentations 134. For example, FIG. 6 illustrates a pledget 20 having a plurality of longitudinal rows of discrete indentations 134. In various aspects, a first row of discrete indentations 134 can be aligned in the circumferential direction 154 with a second row of discrete indentations 134. In some aspects, a first row of discrete indentations 134 can be staggered in the circumferential direction 154 with a second row of discrete indentations 134 as illustrated in FIG. 6. In various aspects, the first and second rows of discrete indentations 134 can be adjacent rows. In some aspects, the longitudinal rows of discrete indentations 134 can extend around the circumferential direction 154 of the pledget 20 and can be staggered such that adjacent rows of discrete indentations 134 are not aligned.

In various aspects, the apparatus of the present disclosure can be used to form one or more longitudinal grooves 158 in the absorbent pledgets 20. For example, FIG. 6 illustrates a pledget 20 having a plurality of longitudinal grooves 158. Likewise, the apparatus of the present disclosure can be used to form a plurality of longitudinal grooves 158 and providing a plurality of longitudinal rows of discrete indentations 134 wherein the longitudinal grooves 158 and the longitudinal rows of discrete indentations 134 are alternated in the circumferential direction 154 of the pledget 20 as illustrated in FIG. 6. The longitudinal grooves 158 can be linear, non-linear, helical, continuous, discontinuous, wide, narrow, any other suitable shape, size, orientation, or any combination of these.

It is believed that this localized (i.e., intermittent) penetration and compression of the absorbent layers displaces absorbent material and creates disruptions to the surface-to-surface interaction between the layers. As such, it is believed that the pledget 20 is better able to withstand withdrawal forces without delaminating, unrolling, unfolding, telescoping, or otherwise structurally degrading. This belief is supported by an experiment wherein a commercially-available radially-wound tampon with compressed grooves was penetrated to 39% of the compressed diameter of 6.6 mm with 56 discrete shaping elements (8 rows of 7 discrete projections each) having an extension dimension of 2.55 mm and a shape such as that illustrated in FIG. 7 to create 56 discrete indentations. This indented tampon was tested against a control tampon with compressed grooves that did not have discrete indentations. The indented tampon was found to have a peak telescoping force that was more than three times the peak telescoping force of the control tampon.

The absorbent blanks 114 and ultimately the pledgets 20 of the present disclosure can include any suitable type and/or combination of absorbent fibers and/or binder fibers. The absorbent fibers can include any suitable absorbent material made from artificial or natural fibers, such as polyester, cellulose, acetate, nylon, polypropylene, rayon, cotton or blends thereof. The absorbent fibers can also include any suitable blend of fibers. For example, the absorbent fibers can be formed from cellulosic fibers, such as cotton and rayon. The absorbent fibers can be 100 wt % cotton, 100 wt % rayon, or a blend of cotton and rayon fibers. In some aspects, the cellulose fibers can be modified for super-absorbency.

In some aspects, the absorbent blanks 114 and ultimately the pledgets 20 can include a combination of absorbent fibers and long binder fibers like those taught in U.S. application Ser. No. 13/051447 to Jackson et al. that was filed on Mar. 18, 2011, and is incorporated herein by reference where not contradictory.

When cotton fibers are used, the cotton fibers should have a staple length of between about 20 millimeters (mm) to about 40 mm. The cotton fibers should generally have a fiber size of between about 15 microns to about 28 microns. The cotton fibers can also be bleached if desired. Bleaching will make the cotton fibers whiter in appearance.

When rayon fibers are present, the rayon fibers should have a staple length of between about 20 mm to about 45 mm. In some aspects, rayon fibers can have a staple length of 38-42 mm. Suitable rayon fibers can have a denier of between about 1 to about 6. In specific aspects, the rayon fibers can be viscose rayon, lyocell rayon, or any other suitable rayon or regenerated cellulose.

The rayon fibers can have a circular, bi-lobal, or tri-lobal cross-sectional configuration, or some other cross-sectional configuration known to those skilled in the art. The bi-lobal configuration has a cross-sectional profile that looks like a dog bone while the tri-lobal configuration has a cross-sectional profile that looks like a "Y". The rayon fibers can also be bleached if desired.

In various aspects, the absorbent blanks 114 can be rolled, stacked, folded, or otherwise manipulated before being compressed into pledgets 20. For example, suitable menstrual tampons can include "cup" shaped pledgets like those disclosed in U.S. Patent Application Publication 2008/0287902 to Edgett and U.S. Pat. No. 2,330,257 to Bailey; "accordion" or "W-folded" pledgets like those disclosed in U.S. Pat. No. 6,837,882 to Agyapong; "radially wound" pledgets like those disclosed in U.S. Pat. No. 6,310,269 to Friese; "sausage" type or "wad" type pledgets like those disclosed in U.S. Pat. No. 2,464,310 to Harwood; "M-folded" tampon pledgets like those disclosed in U.S. Pat. No. 6,039,716 to Jessup; "stacked" tampon pledgets like those disclosed in U.S. Patent Application Publication 2008/0132868 to Jorgensen; or "bag" type tampon pledgets like those disclosed in U.S. Pat. No. 3,815,601 to Schaefer.

A suitable method for making "radial wound" pledgets is disclosed in U.S. Pat. No. 4,816,100 to Friese. Suitable methods for making "W-folded" pledgets are disclosed in U.S. Pat. No. 6,740,070 to Agyapong; U.S. Pat. No. 7,677,189 to Kondo; and U.S. Patent Application Publication 2010/0114054 to Mueller. A suitable method for making "cup" pledgets and "stacked" pledgets is disclosed in U.S. Patent Application Publication 2008/0132868 to Jorgensen.

In various aspects, the tampons 10 of the present disclosure can also include a cover material disposed over at least a portion of the outer surface. The cover can be beneficial in assuring that the fibers of the pledget 20 do not directly contact the inner walls of a woman's vagina. This minimizes the likelihood that fibers will be left behind in the vagina after the tampon 10 has been removed. The cover can be tucked into the insertion end 38 and/or the withdrawal end 42 so as to substantially or completely surround and enclose the absorbent fibers. The cover can also be constructed from a heat-sealable material to assist in bonding all or portions of it to the pledget 20, such as by heat and/or pressure.

The optional cover can be formed from a nonwoven material such as a polyolefin, particularly polypropylene or polyethylene. The cover material can be spunbond. In some aspects, the cover material can be a bonded carded web made of bicomponent fibers (e.g., polyethylene/polyethylene terephthalate sheath core). In some aspects, the cover material can be a film material made from polypropylene, polyethylene, or a combination of both. For example, in some aspects, the cover can have three layers made of polyethylene-polypropylene-polyethylene. In some aspects, the cover material can have apertures having a diameter of 1 mm or less or 0.5 mm or less.

In various aspects, the withdrawal string 21 can be attached to the pledget 20 in any suitable manner. For example, an opening can be formed through the pledget 20 (and cover if provided) so as to provide a means for attaching a withdrawal string 21. In various aspects, the withdrawal string 21 can be attached to the absorbent blank 114 before or after it is compressed into the pledget 20. The withdrawal string 21 can be attached to the pledget 20 and then looped upon itself. A knot 31 can then be formed near the free ends of the withdrawal string 21 to assure that the string 21 does not separate from the pledget 20. The knot 31 also serves to prevent fraying of the withdrawal string 21 and to provide a place or point where a woman can grasp the withdrawal string 21 when she is ready to remove the tampon 10 from her vagina.

The withdrawal string 21 can be constructed from various types of threads or ribbons. A thread or ribbon can be made from 100 percent cotton fibers and/or other materials in whole or part. In some aspects, the withdrawal string 21 can be 67% polyethylene terephthalate and 33% rayon. The withdrawal string 21 can be bonded to the absorbent blank 114 and/or the pledget 20 with or without tying. The withdrawal string 21 can have any suitable length and/or the withdrawal string 21 can be dyed and/or treated with an anti-wicking agent, such as wax, before being secured to the pledget 20.

While the disclosure has been described in detail with respect to specific aspects thereof, it will be appreciated that those skilled in the art, upon attaining understanding of the foregoing will readily appreciate alterations to, variations of, and equivalents to these aspects. Accordingly, the scope of the present disclosure should be assessed as that of the appended claims and any equivalents thereto. Additionally, all combinations and/or sub-combinations of the disclosed aspects, ranges, examples, and alternatives are also contemplated.

The invention claimed is:

1. An apparatus for compressing a material, the apparatus having a central longitudinal axis and comprising:
   a plurality of levers, each lever comprising a lever outer end and a radially-inward end portion and a lever longitudinal axis extending from the lever outer end to the radially-inward end portion;
   a plurality of jaws, wherein each jaw is attached to a lever, and wherein each jaw has a compression surface having an area and wherein the compression surface defines a plane that is generally parallel to the lever longitudinal axis;
   a compressing mechanism configured to move each lever in a non-linear motion such that the area of a compression surface exposed to the material decreases with the inward movement of that compression surface; and
   a shaping element associated with at least one compression surface.

2. The apparatus of claim 1, wherein each jaw is integral with a lever.

3. The apparatus of claim 1, wherein each jaw is attached to a lever to form a lever/jaw combination, and wherein each lever/jaw combination includes a biasing mechanism configured such that adjacent jaws contact each other.

4. The apparatus of claim 1, further comprising a gap between adjacent jaws, the gap having a gap centerline, wherein a line including the gap centerline of the gap between adjacent jaws is parallel to the compression surface of the adjacent jaw.

5. The apparatus of claim 1, further comprising a plurality of shaping elements on each compression surface.

6. The apparatus of claim 1, wherein each jaw with a shaping element is identical.

7. The apparatus of claim 1, wherein the shaping element is a pin.

8. The apparatus of claim 7, wherein the pin is one of cylindrical, conical, and elliptical.

9. The apparatus of claim 1, wherein the shaping element is configured to impart a helical groove in the material.

10. The apparatus of claim 1, further comprising a plurality of shaping elements configured to impart a pattern in the material.

11. The apparatus of claim 1, wherein the shaping element includes a cross-section, and wherein the cross-section is one of bulbous, rectilinear, trapezoidal, polygonal, and triangular.

12. The apparatus of claim 1, wherein the orientation of the shaping element with respect to the apparatus central longitudinal axis is generally parallel, perpendicular, angled, or a combination of these.

13. The apparatus of claim 1, further comprising a plurality of shaping elements configured to impart a circumferential groove in the material.

14. The apparatus of claim 1, wherein the shaping element is a cavity in the compression surface.

15. The apparatus of claim 14, wherein at least a portion of the compression surface is a curvilinear surface.

16. The apparatus of claim 1, wherein the material has an initial compression diameter and a final compression diameter, and wherein the ratio of the initial compression diameter to the final compression diameter obtainable with the apparatus is greater than two.

17. The apparatus of claim 1, wherein the material has an initial compression diameter and a final compression diameter, and wherein the ratio of the initial compression diameter to the final compression diameter obtainable with the apparatus is greater than five.

18. An apparatus for compressing a material, the apparatus having a central longitudinal axis and comprising:
   a plurality of levers, each lever comprising a lever outer end and a radially-inward end portion and a lever longitudinal axis extending from the lever outer end to the radially-inward end portion;
   a plurality of jaws, wherein each jaw is attached to a lever, and wherein each jaw has a compression surface having an area and wherein the compression surface defines a plane that is generally parallel to the lever longitudinal axis;
   a compressing mechanism configured to move each lever in a non-linear motion such that the area of a compression surface exposed to the material decreases with the inward movement of that compression surface; and
   a plurality of shaping elements projecting from at least one compression surface, wherein the plurality of shaping elements is configured to impart a pattern in the material.

19. An apparatus for compressing a material, the apparatus having a central longitudinal axis and comprising:
   a plurality of levers, each layer comprising a lever outer end and a radially-inward end portion and a lever longitudinal axis extending from the lever outer end to the radially-inward end portion;
   a plurality of jaws, wherein each jaw is attached to a lever, and wherein each jaw has a compression surface having an area;
   a compressing mechanism configured to move each lever in a non-linear motion such that the area of a compression surface exposed to the material decreases with the inward movement of that compression surface and wherein the compression surface defines a plane that is generally parallel to the lever longitudinal axis; and
   a plurality of shaping elements each projecting from a compression surface, wherein the plurality of shaping elements is configured to impart a plurality of grooves in the material.

* * * * *